United States Patent [19]

Canich

[11] Patent Number: 5,504,169

[45] Date of Patent: *Apr. 2, 1996

[54] PROCESS FOR PRODUCING AMORPHOUS POLY-α-OLEFINS WITH A MONOCYCLOPENTADIENYL TRANSITION METAL CATALYST SYSTEM

[75] Inventor: Jo Ann M. Canich, Webster, Tex.

[73] Assignee: Exxon Chemical Patents Inc., Wilmington, Del.

[ * ] Notice: The term of this patent shall not extend beyond the expiration date of Pat. No. 5,420,217.

[21] Appl. No.: 395,544

[22] Filed: Feb. 28, 1995

Related U.S. Application Data

[60] Continuation-in-part of Ser. No. 159,888, Nov. 30, 1993, Pat. No. 5,420,217, which is a division of Ser. No. 902,631, Jun. 23, 1992, abandoned, which is a continuation-in-part of Ser. No. 720,282, Jun. 24, 1991, abandoned, which is a division of Ser. No. 581,817, Sep. 13, 1990, Pat. No. 5,026,798, which is a continuation-in-part of Ser. No. 533,245, Jun. 4, 1990, Pat. No. 5,055,438, which is a continuation-in-part of Ser. No. 406,945, Sep. 13, 1989, abandoned.

[51] Int. Cl.⁶ .................................................. C08F 4/642

[52] U.S. Cl. .................... 526/127; 526/160; 526/161; 526/351; 502/117; 502/155

[58] Field of Search .................... 526/127, 160, 526/351

[56] References Cited

FOREIGN PATENT DOCUMENTS

| | | |
|---|---|---|
| 475306 | 3/1992 | European Pat. Off. . |
| 0475306 | 3/1992 | European Pat. Off. . |
| 0604908 | 7/1994 | European Pat. Off. . |
| 0604917 | 7/1994 | European Pat. Off. . |
| 604908 | 7/1994 | European Pat. Off. . |
| 03887 | 7/1987 | WIPO . |

OTHER PUBLICATIONS

Dale S. Pearson, et al., Rheological Properties of Poly(1,3-dimethyl-1-butenylene) and Model Atactic Polypropylene, 21 Macromolecules, 478–484 (1988).

*Primary Examiner*—David W Wu
*Attorney, Agent, or Firm*—Catherine L. Bell; C. Paige Schmidt

[57] ABSTRACT

The invention is a catalytic process using a Group IV B transition metal component and a cocatalyst or activator component to polymerize α-olefins to produce amorphous poly-α-olefins having high molecular weight.

9 Claims, No Drawings

PROCESS FOR PRODUCING AMORPHOUS POLY-α-OLEFINS WITH A MONOCYCLOPENTADIENYL TRANSITION METAL CATALYST SYSTEM

SPECIFICATION

This application is a continuation-in-part of U.S. patent application Ser. No. 08/159,888 filed on Nov. 30, 1993, now U.S. Pat. No. 5,420,217, which is a divisional of U.S. patent application Ser. No. 902,631, filed Jun. 23, 1992, now abandoned, which is a continuation-in-part of U.S. patent application Ser. No. 720,282, filed on Jun. 24, 1991, now abandoned which is a divisional of application Ser. No. 07/581,817, filed on Sep. 13, 1990, now U.S. Pat. No. 5,026,798, which issued Jun. 25, 1990, which is a continuation-in-part of U.S. patent application Ser. No. 533,245, filed Jun. 4, 1990, now U.S. Pat. No. 5,055,438, which in turn is a continuation-in-part of U.S. patent application Ser. No. 406,945, filed Sep. 13, 1989, now abandoned. All of the above patent applications are hereby incorporated by reference.

FIELD OF THE INVENTION

This invention relates to a process for polymerizing α-olefins which utilizes certain monocyclopentadienyl metal compounds of a Group IV B transition metal of the Periodic Table of Elements in an activated catalyst system to produce, amorphous, low crystallinity poly-α-olefins, particularly polypropylene and α-olefin copolymers of propylene. In U.S. Pat. No. 5,026,798 an invention was disclosed and claimed for a process for the production of crystalline poly-α-olefins. It has further been discovered that by careful choice of the components of the monocyclopentadienyl metal compounds, the same process can also be used to elegantly produce amorphous poly-α-olefins that may have stereoregular regions within the polymer chain.

BACKGROUND OF THE INVENTION

As is well known, various processes and catalysts exist for the homopolymerization or copolymerization of olefins. For some applications it is of primary importance for a polyolefin to have a high weight average molecular weight while having a relatively narrow molecular weight distribution. A high weight average molecular weight, ($M_w$), when accompanied by a narrow molecular weight distribution, (MWD), provides a polyolefin with high strength properties. For other applications, such as compatibilization or adhesion, a low or medium weight average $M_w$ with a relatively narrow MWD is a primary concern.

Traditional Ziegler-Natta catalysts systems—a transition metal compound cocatalyzed by an aluminum alkyl—are capable of producing polyolefins having a high or low molecular weight but a broad molecular weight distribution.

More recently a catalyst system has been developed wherein the transition metal compound has two or more cyclopentadienyl ring ligands—such transition metal compound being referred to herein as a "metallocene"—which catalyzes the production of olefin monomers to polyolefins. Accordingly, titanocenes and zirconocenes, have been utilized as the transition metal component in such "metallocene" containing catalyst systems for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for the production of polyolefins.

It is also now known that metallocenes may be cocatalyzed or activated with an ionic activator such as described in U.S. patent application Ser. Nos. 133,052, 133,480, and 542,236 herein fully incorporated by reference and U.S. Pat. No. 5,384,299 herein fully incorporated by reference.

Generally these ionic activators comprise a cation which will irreversibly react with at least one ligand contained in the metallocene, and a non-coordinating anion which is bulky, labile and stable. The cation reacts with the metallocene ligand thereby generating an ion pair consisting of a metallocene cation and the non-coordinating anion. Other methods of generating the ion pair are known in the art and are suitable for use with the present invention.

The zirconocenes, as cocatalyzed or activated with an alumoxane, are commonly more active than their hafnium or titanium analogues for the polymerization of ethylene alone or together with an α-olefin comonomer. When employed in a non-supported form—i.e., as a homogeneous or soluble catalyst system—to obtain a satisfactory rate of productivity even with the most active zirconocene species typically requires the use of a quantity of alumoxane activator sufficient to provide an aluminum atom to transition metal atom ratio (Al:TM) of at least greater than 1000:1; often greater than 5000:1, and frequently on the order of 10,000:1. Such quantities of alumoxane impart to a polymer produced with such catalyst system an undesirable content of catalyst metal residue, i.e., an undesirable "ash" content (the nonvolatile metal content). In high pressure polymerization procedures using soluble catalyst systems wherein the reactor pressure exceeds about 500 bar only the zirconium or hafnium species of metallocenes may be used.

Titanium species of metallocenes are generally unstable at such high pressures unless deposited upon a catalyst support. A wide variety of Group IV B transition metal compounds have been named as possible candidates for an alumoxane cocatalyzed catalyst system. Although bis(cyclopentadienyl) Group IV B transition metal compounds have been the most preferred and heavily investigated for use in alumoxane activated catalyst systems for polyolefin production, suggestions have appeared that mono and tris(cyclopentadienyl) transition metal compounds may also be useful. See, for example U.S. Pat. Nos. 4,522,982; 4,530,914 and 4,701,431. Such mono(cyclopentadienyl) transition metal compounds as have heretofore been suggested as candidates for an alumoxane activated catalyst system are mono(cyclopentadienyl) transition metal trihalides and trialkyls.

More recently, International Publication No. WO 87/03887 describes the use of a composition comprising a transition metal coordinated to at least one cyclopentadienyl and at least one heteroatom ligand as a transition metal component for use in an alumoxane activated catalyst system for α-olefin polymerization. The composition is broadly defined as a transition metal, preferably of Group IV B of the Periodic Table, which is coordinated with at least one cyclopentadienyl ligand and one to three heteroatom ligands, the balance of the transition metal coordination requirement being satisfied with cyclopentadienyl or hydrocarbyl ligands. Catalyst systems described by this reference are illustrated solely with reference to transition metal compounds which are metallocenes, i.e., bis(cyclopentadienyl) Group IV B transition metal compounds.

Even more recently, at the Third Chemical Congress of North American held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such monocyclopentadienyl transition metal compound could be usefully employed for commercial polymerization processes.

A need still exists for discovering catalyst systems that permit the selective production of higher or lower molecular weight polyolefins and desirably with a narrow molecular weight distribution. It is further desirable that a catalyst be discovered which will be capable of catalyzing the polymerization of α-olefin monomer(s) to produce a stereoregular low crystallinity or amorphous form of poly-α-olefin when desired.

There are at least three different types of stereoregular polymers. These polymers are comprised of α-olefin monomers where hydrocarbyl groups are pendant from the polymer backbone chain. Relative to the polymer backbone chain, the pendant hydrocarbyl groups may be arranged in different stereochemical configurations which are denominated as, for example, atactic, isotactic, or syndiotactic pendant group configuration.

The degree and type of tacticity of a polyolefin molecule are critical determinants of the physical properties which a resin composed of such polymer molecules will exhibit. Other critical determinants of the properties which a resin will exhibit are the type and relative concentration of monomers and comonomers, the weight average molecular weight ($M_w$) of the polymer molecules comprising the resin bulk, the molecular weight distribution (MWD) and the composition distribution of the resin.

Important from a commercial standpoint is the rate or productivity at which a catalyst system will produce a poly-α-olefin resin of a desired set of properties in terms of tacticity, weight average molecular weight and molecular weight distribution.

The weight average molecular weight ($M_w$) of a poly-α-olefin is an important physical property determinant of the practical uses to which such polymer can be put. For end use applications which require high strength and low creep, the $M_w$ of such a resin must generally be in excess of 100,000, preferably in excess of 200,000. Where the $M_w$ is lower than 100,000 the polymer can be used for other applications such as adhesives and compatibilizers. Further, for such high strength applications, the poly-α-olefin resin must generally have a high degree of crystallinity. Low crystallinity and amorphous poly-α-olefins are useful in adhesive compositions, in compatibilizing applications, as additives, etc. The degree of crystallinity which a poly-α-olefin is capable of obtaining is, in major part, determined by the stereochemical regularity of the hydrocarbyl groups which are pendent to the polymer molecule backbone, i.e., the tacticity of the polymer.

Five types of tacticity have been described in poly-α-olefins: atactic, normal isotactic, isotactic stereoblock, syndiotactic, and hemiisotactic. Although all of these tacticity configurations have been primarily demonstrated in the case of polypropylene, in theory each is equally possible for polymers comprised of any α-olefin, cyclic olefin or internal olefin.

Atactic poly-α-olefins are those wherein the hydrocarbyl groups pendent to the polymer molecule backbone assume no regular order with reference to the backbone. This random, or atactic, structure is represented by a polymer backbone of alternating methylene and methine carbons, with randomly oriented branches substituting the methine carbons. The methine carbons randomly have R and S configurations, creating adjacent pairs either of like configuration (a "meso" or "m" dyad) or of unlike configuration (a "racemic" or "r" dyad). The atactic form of a polymer contains approximately equal fractions of meso and racemic dyads.

Atactic poly-α-olefins, particularly atactic polypropylene, are soluble in aliphatic and aromatic solvents at ambient temperature. Since atactic polymers exhibit no regular order or repeating unit configurations in the polymer chain, such atactic polymers are amorphous materials. An amorphous material tends to lack a molecular lattice structure and have poorly defined melting points. Thus typical atactic poly-α-olefins are amorphous, and generally have no measurable melting point. Atactic polymers exhibit little if any crystallinity, hence they are generally unsuitable for high strength applications regardless of the weight average molecular weight of the resin.

Isotactic poly-α-olefins are those wherein the pendent hydrocarbyl groups are ordered in space to the same side or plane of the polymer backbone chain. Using isotactic polypropylene as an example, the isotactic structure is typically described as having the pendent methyl groups attached to the ternary carbon atoms of successive monomeric units on the same side of a hypothetical plane through the carbon backbone chain of the polymer, e.g., the methyl groups are all above or below the plane as shown below.

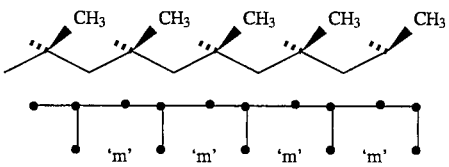

The degree of isotactic regularity may be measured by NMR techniques. Bovey's NMR nomenclature for an isotactic pentad is . . . mmmm . . . with each "m" representing a "meso" dyad or successive methyl groups on the same side in the plane.

In the normal isotactic structure of a poly-α-olefin, all of the monomer units have the same stereochemical configuration, with the exception of random errors which appear along the polymer. Such random errors almost always appear as isolated inversions of configuration which are corrected in the very next α-olefin monomer insertion to restore the original R or S configuration of the propagating polymer chain. Single insertions of inverted configuration give rise to rr triads, which distinguish this isotactic structure in its NMR from the isotactic stereoblock form.

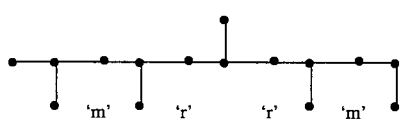

As is known in the art, any deviation or inversion in the regularity of the structure of the chains lowers the degree of isotacticity and hence the crystallinity of which the polymer is capable. There are two other types of "errors" which have been observed in isotactic polymers prepared using metallocene based catalyst systems which act to lower the melting point and/or Tg of the material. These errors, as shown below arise when a monomer is added to the growing polymer chain in a 1,3 or 2,1 fashion.

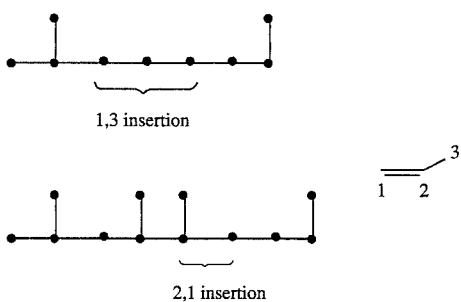

1,3 insertion

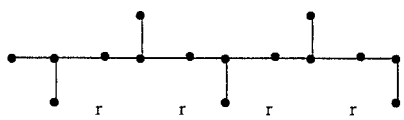

2,1 insertion

Long before anyone had discovered a catalyst system which produced the isotactic stereoblock form of a poly-α-olefin, the possible existence of a polymer of such microstructure had been recognized and mechanisms for its formation had been proposed based on conventional Ziegler-Natta mechanisms in Langer, A. W., *Lect. Bienn. Polym. Symp.* 7th (1974); *Ann. N.Y. Acad. Sci.* 295, 110–126 (1977). The first example of this form of polypropylene and a catalyst which produces it in a pure form were reported in U.S. Pat. No. 4,522,982. The formation of stereoblock isotactic polymer differs from the formation of the normal isotactic structure in the way that the propagation site reacts to a stereochemical error in the chain. As mentioned above, the normal isotactic chain will return to the original configuration following an error because the stereochemical regulator, the catalytic active metal species and its surrounding ligands, continue to dictate the same stereochemical preference during monomer insertion. In stereoblock propagation, the catalytic active metal site itself changes from one which dictates a monomer insertion of R configuration to one which dictates an S configuration for monomer insertion. The isotactic stereoblock form is shown below.

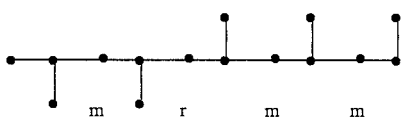

This occurs either because the metal and its ligands change to the opposite stereochemical configuration or because the configuration of the last added monomer, rather than the metal chirality, controls the configuration of the next added monomer. In Ziegler-Natta catalysts, including the above referenced system, the exact structure and dynamic properties of the active site are not well understood, and it is virtually impossible to distinguish between the "site chirality exchange" and "chain end control" mechanisms for the formation of isotactic stereoblock poly-α-olefins.

Unlike normal isotactic polymers, the lengths of individual blocks of the same configuration in the stereoblock structure vary widely due to changing reaction conditions. Since only the erroneous parts of the chains affect the crystallinity of the resin product, in general, normal isotactic polymers and isotactic stereoblock polymers of long block length (greater than 50 isotactic placements) have similar properties.

Highly isotactic poly-α-olefins are insoluble in xylene and are capable of exhibiting a high degree of crystallinity and are in part characterizable by their melting point temperature. Accordingly, isotactic poly-α-olefins are, depending upon their weight average molecular weight exceeding about 100,000, well suited to high strength end use applications.

Syndiotactic poly-α-olefins are those wherein the hydrocarbyl groups pendent to the polymer molecular backbone alternate sequentially in order from one side or plane to the opposite side or plane relative to the polymer backbone, as shown below.

In NMR nomenclature, this pentad is described as . . . rrrr . . . in which each r represents a "racemic" dyad, i.e., successive methyl groups on alternate sides of the plane. The percentage of r dyads in the chain determines the degree of syndiotacticity of the polymer.

Syndiotactic propagation has been studied for over 25 years; however, only a few good syndiospecific catalysts have been discovered, all of which are extremely sensitive to monomer bulkiness. As a result, well-characterized syndiotactic polymers are limited only to polypropylenes. The molecular chain backbone of a syndiotactic polymer can be considered to be a copolymer of olefins with alternating stereochemical configurations. Highly syndiotactic polymers are generally highly crystalline and will frequently have high melting points similar to their isotactic polymorphs.

Like isotactic poly-α-olefins, syndiotactic poly-α-olefins are capable of exhibiting a high degree of crystallinity, hence are suitable for high strength applications provided their $M_w$ exceeds about 100,000. Syndiotactic poly-α-olefins are in part characterized by their exhibition of a melting point temperature.

Amorphous poly-α-olefins, generally regarded to be atactic, noncrystalline and lacking in a molecular lattice structure which is characteristic of the solid state, tend to lack well defined melting points. Such amorphous poly-α-olefins have uses in adhesives and as compatibilizers among other things.

For any of the above described materials the final resin properties and their suitability for particular applications depends on the type of tacticity (stereoregularity), the melting point, the average molecular weight, the molecular weight distribution, the type and level of monomer and comonomer, the sequence distribution, and the presence or absence of head or end group functionality. Accordingly, the catalyst system by which such a stereoregular poly-α-olefin resin is to be produced should, desirably, be versatile in terms of $M_w$, MWD, tacticity type and level, and comonomer choice. Further, the catalyst system should be capable of producing these polymers with or without head and/or end group functionality, such as olefinic unsaturation. Still further, such catalyst system must be capable, as a commercially practical constraint, of producing such resins at an acceptable production rate. Most preferably, the catalyst system should be one which, at its productivity rate, provides a resin product which does not require a subsequent treatment to remove catalyst residue to a level which is acceptable for the resin in the end use application desired. Finally, an important feature of a commercial catalyst system is its adaptability to a variety of processes and conditions.

Conventional titanium based Ziegler-Natta catalysts for the preparation of isotactic polymers are well known in the art. These commercial catalysts are well suited for the production of highly crystalline, high molecular weight materials. The systems are, however, limited in terms of molecular weight, molecular weight distribution, and tacticity control. The fact that the conventional catalysts contain several types of active sites further limits their ability to control the composition distribution in copolymerization.

More recently a new method of producing isotactic polymers from an alumoxane cocatalyzed, or activated, metallocene which in its natural state has chirality centered at the transition metal of the metallocene, was reported in Ewen, J. A., *J. Amer. Chem. Soc.*, v. 106, p. 6355 (1984) and Kaminsky, W., et al., *Angew. Chem. Int. Ed. Eng.*; 24, 507–8 (1985).

Catalysts that produce isotactic polyolefins are also disclosed in U.S. Pat. No. 4,794,096. This patent discloses a chiral, stereorigid metallocene catalyst which is activated by either an alumoxane or ionic cocatalyst which is reported to polymerize olefins to isotactic or atactic polyolefin forms. alumoxane cocatalyzed metallocene structures which have been reported to polymerize stereoregularly are the ethylene bridged bis-indenyl and bis-tetra-hydroindenyl titanium and zirconium (IV) catalyst. Such catalyst systems were synthesized and studied in Wild et al., *J. Organomet. Chem.* 232, 233–47 (1982), and were later reported in Ewen and Kaminsky et al., mentioned above, to polymerize α-olefins stereoregularly. Further reported in West German Off DE 3443087A1 (1986), but without giving experimental verification, is that the bridge length of such stereorigid metallocenes can vary from a $C_1$ to $C_4$ hydrocarbon and the metallocene rings can be simple or bi-cyclic but must be asymmetric.

Alumoxane activated metallocene catalysts generally require a high content of alumoxane cocatalyst to be sufficiently productive for commercial use. Accordingly, metallocene-alumoxane produced isotactic poly-α-olefin resins generally have a higher than desired catalyst residue content. Hafnocene systems, which yield polymers of higher average $M_w$ than the zirconium analogues, have very low activities even at high alumoxane concentrations.

Metallocenes may also be cocatalyzed or activated with an ionic activator such as described in U.S. Pat. No. 5,278,119 and EP 277 003 herein fully incorporated by reference and U.S. Pat. No. 5,384,299 herein fully incorporated by reference.

Generally these ionic activators comprise a cation which will irreversibly react with at least one ligand contained in the metallocene and a non-coordinating anion which is bulky, labile and stable. The cation reacts with the one metallocene ligand thereby generating an ion pair consisting of a metallocene cation and the non-coordinating anion. Other methods of generating the ion pair are known in the art and are suitable for use with the present invention.

Syndiotactic polyolefins were first disclosed by Natta et al. in U.S. Pat. No. 3,258,455. As reported, Natta obtained syndiotactic polypropylene by using a catalyst prepared from titanium trichloride and diethyl aluminum monochloride. A later patent to Natta et al., U.S. Pat. No. 3,305,538, discloses the use of vanadium triacetylacetonate or halogenated vanadium compounds in combinations with organic aluminum compounds for production of syndiotactic polypropylene.

More recently, a metallocene based catalyst system has been disclosed which is stated to be capable of production of syndiotactic polypropylene of high stereoregularity. U.S. Pat. No. 4,892,851 describes catalyst systems consisting of a bridged metallocene having at least two differently substituted cyclopentadienyl ring ligands which, when cocatalyzed with an alumoxane, is stated to be capable of production of syndiotactic polypropylene. Again, in commercial production to obtain a sufficient productivity level with such catalyst system, the content of alumoxane is undesirably high and consequently the catalyst residue in the resin so produced is undesirably high.

Generally metallocene catalyst systems produce polymer having characteristics ($M_w$, MWD, tacticity type, comonomer incorporation, etc.) that are controlled either by modifications to the structure of the metallocene ligand(s) or by adjustment of the process conditions (temperature, pressure, concentrations). In general, adjustment of process conditions does not allow independent control of tacticity level, $M_w$ and comonomer content. Addition of chain transfer agents such as hydrogen gas to the reactor gives lower molecular weight products without affecting tacticity, however, the resulting polymer no longer has unsaturated end groups. End group functionalization is often an important feature in the application of low molecular weight polymers. Given these limitations, one must prepare a wide variety of differently substituted metallocene precursors to access the entire range of desired materials.

In view of the difficulty and practical limitations in the synthesis of bridged metallocene complexes necessary for the production of a metallocene catalyst system capable of producing poly-α-olefins, it would be desirable to develop new catalytic processes which could produce high or low molecular weight, tactic, amorphous poly-α-olefins or low crystallinity poly-α-olefins of relatively narrow MWD.

SUMMARY OF THE INVENTION

The process of this invention employs a metallocene such as that previously disclosed in U.S. Pat. No. 5,055,438, issued Oct. 8, 1991, and herein incorporated by reference, which is comprised of a transition metal component from Group IV B of the Periodic Table of the Elements (*CRC Handbook of Chemistry and Physics*, 68th ed. 1987–1988) ("metallocene") and a cocatalyst or activator component. The catalyst system may be employed in solution, slurry, gas phase or bulk phase polymerization procedure to produce poly-α-olefins of high or low weight average molecular weight (as used herein, all references to molecular weight refer to weight average molecular weight unless specifically indicated otherwise) and relatively narrow molecular weight distribution. The present invention relates to using such catalysts of U.S. Pat. No. 5,055,438 to produce atactic amorphous poly-α-olefins of high or low molecular weight, preferably high molecular weight and narrow MWD.

Atactic, amorphous poly-α-olefin is herein defined to mean a poly-α-olefin that lacks or has a poorly defined melting point and may or may not have low amounts of crystallinity. The amorphous product of this invention is substantially, preferably completely, atactic. Stereoblock forms of poly-α-olefin as defined above are excluded from this definition. The amorphous polymers of this invention typically have a melting point of less than or equal to about 2 J/g.

The catalyst of this invention comprises a Group IV B transition metal component (metallocene) and an activator or cocatalyst. The metallocene of the catalyst system is represented by the formula:

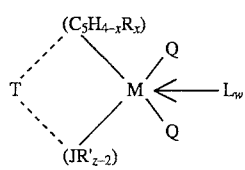

wherein: M is Zr, Hf or Ti in its highest formal oxidation state (+4, $d^0$ complex);

$(C_5H_{4-x}R_x)$ is a cyclopentadienyl ring which is symmetrically substituted with from zero to four substituent groups R, "x" is 0, 1, 2, 3, or 4 denoting the degree of substitution, and each substituent group R is, independently, a radical selected from a group consisting of $C_1$-$C_{20}$ hydrocarbyl radicals, substituted $C_1$-$C_{20}$ hydrocarbyl radicals wherein one or more hydrogen atoms is replaced by a halogen radical, an amido radical, a phosphido radical, an alkoxy radical or any other radical containing a Lewis acidic or basic functionality, $C_1$-$C_{20}$ hydrocarbyl-substituted metalloid radicals wherein the metalloid is selected from the Group IV A of the Periodic Table of Elements; and halogen radicals, amido radicals, phosphido radicals, alkoxy radicals, aklylborido radicals or any other radical containing Lewis acidic or basic functionality; or $(C_5H_{4-x}R_x)$ is a cyclopentadienyl ring in which at least two adjacent R-groups are joined forming a $C_4$-$C_{20}$ ring to give a saturated or unsaturated polycyclic cyclopentadienyl ligand such as indenyl, tetrahydroindenyl. Symmetrical substitution exists when two R groups of approximately equal steric bulk are substituted at symmetric sites, i.e. 2,5; 3,4; etc.). A $C_4$-$C_{20}$ ring can be considered symmetrically balanced with the bridging group, T.

$(JR'_{z-2})$ is a heteroatom ligand in which J is an element with a coordination number of three from Group V A or an element with a coordination number of two from Group VI A of the Periodic Table of Elements, preferably nitrogen, phosphorus, oxygen or sulfur, and each R' is, independently a radical selected from a group consisting of $C_1$-$C_{20}$ hydrocarbyl radicals, substituted $C_1$-$C_{20}$ hydrocarbyl radicals wherein one or more hydrogen atoms are replaced by a halogen radical, an amido radical, a phosphido radical, an alkoxy radical or any other radical containing a Lewis acidic or basic functionality, and "z" is the coordination number of the element J;

each Q may be independently any univalent anionic ligand such as a halide, hydride, or substituted or unsubstituted $C_1$-$C_{20}$ hydrocarbyl, alkoxide, aryloxide, amide, or phosphide, provided that where any Q is a hydrocarbyl such Q is not a cyclopentadienyl or substituted cyclopentadienyl ligand, or both Q together may be an alkylidene or a cyclometallated hydrocarbyl or any other divalent anionic chelating ligand and provided that when an ionic activator is used, Q is hydride or substituted or unsubstituted $C_1$-$C_{20}$ hydrocarbyl, or, alternatively, the transition metal compound is additionally contacted with an alkylating reagent such as an alumoxane or aluminum alkyl;

T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

L is a neutral Lewis base such as diethylether, tetraethylammonium chloride, tetrahydrofuran, dimethylaniline, aniline, trimethylphosphine, n-butylamine, and the like; and "w" is a number from 0 to 3. L can also be a second transition metal compound of the same type such that the two metal centers M and M" are bridged by Q and Q", wherein M" has the same meaning as M and Q" has the same meaning as Q. Such dimeric compounds are represented by the formula:

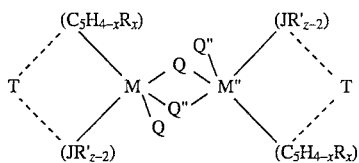

When an alumoxane is used as the cocatalyst component, it may be represented by the formulas: $(R^3\text{-}Al\text{-}O)$ m; $R^4(R^5\text{-}Al\text{-}O)_m AlR^6_2$ or mixtures thereof, wherein $R^3$-$R^6$ are, independently, a $C_1$-$C_5$ alkyl group or halide and "m" is an integer ranging from 1 to about 50 and preferably is from about 13 to about 25.

Catalyst systems of the invention may be prepared by placing the "Group IV B transition metal component" and the alumoxane component in common solution in a normally liquid alkane or aromatic solvent, which solvent is preferably suitable for use as a polymerization diluent for the liquid phase polymerization of an α-olefin monomer.

Those species of the Group IV B transition metal component wherein the metal is titanium have been found to impart beneficial properties to a catalyst system which are unexpected in view of what is known about the properties of bis(cyclopentadienyl) titanium compounds. Whereas titanocenes in their soluble form are generally unstable in the presence of aluminum alkyls, the monocyclopentadienyl titanium metal components of this invention, particularly those wherein the heteroatom is nitrogen, generally exhibit greater stability in the presence of aluminum alkyls and higher catalyst activity rates.

Further, the titanium species of the Group IV B transition metal component catalyst of this invention generally exhibit higher catalyst activities and the production of poly-α-olefins of greater molecular weight than catalyst systems prepared with the zirconium or hafnium species of the Group IV B transition metal component.

A typical polymerization process of the invention such as for the polymerization or copolymerization of propylene or ethylene comprises the steps of contacting propylene, ethylene or other $C_4$-$C_{20}$ α-olefins alone, or with other unsaturated monomers including $C_3$-$C_{20}$ α-olefins, $C_4$-$C_{20}$ diolefins, and/or acetylenically unsaturated monomers either alone or in combination with other olefins and/or other unsaturated monomers, with a catalyst comprising, in a suitable polymerization diluent, a Group IV B transition metal component illustrated above; and a methylalumoxane in an amount to provide a molar aluminum to transition metal ratio of from about 1:1 to about 20,000:1 or more; and reacting such monomer in the presence of such catalyst system at a temperature of from about −100° C. to about 300° C. for a time of from about 1 second to about 10 hours to produce a poly-α-olefin having a weight average molecular weight of from about 1,000 or less to about 200,000 or more, preferably 500,000 or more and a molecular weight distribution of from about 1.5 to about 15.0, preferably from about 1.5 to about 4.0, even more preferably from about 1.5 to about 3.3.

As discussed further hereafter, by proper selection of the type and pattern R substituents for the cyclopentadienyl ligand in relationship to the type of R' substituent of the heteroatom ligand, the transition metal component for the catalyst system may be tailored to function in the catalyst system to produce low crystallinity poly-α-olefins or tactic amorphous poly-α-olefins.

DETAILED DESCRIPTION

Catalyst Component

The Group IV B transition metal component of the catalyst system is represented by the general formula:

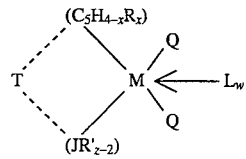

wherein M is Zr, Hf or Ti in its highest formal oxidation state (+4, $d^0$ complex);

$(C_5H_{4-x}R_x)$ is a cyclopentadienyl ring which is symmetrically substituted with from zero to four substituent groups R, "x" is 0, 1, 2, 3, or 4 denoting the degree of substitution, and each substituent group R is, independently, a radical selected from a group consisting of $C_1$-$C_{20}$ hydrocarbyl radicals, substituted $C_1$-$C_{20}$ hydrocarbyl radicals wherein one or more hydrogen atoms is replaced by a halogen radical, an amido radical, a phosphido radicals, and alkoxy radical or any other radical containing a Lewis acidic or basic functionality, $C_1$-$C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals or any other radical containing Lewis acidic or basic functionality; or $(C_5H_{4-x}R_x)$ is a cyclopentadienyl ring in which two adjacent R-groups are joined forming $C_4$-$C_{20}$ ring to give a saturated or unsaturated polycyclic cyclopentadienyl ligand.

Symmetrically substituted is defined to mean that the cyclopentadienyl ring is substituted with R groups that are of approximately the same steric bulk. Typically the size of these R groups are within 2 carbons of each other. However, if two adjacent R groups are linked to form a ring, then the bridge (T) may function as the other "part" of the symmetrical "pair." Likewise, the cyclopentadienyl ring may be substituted at all four sites with R groups and be considered symmetric as long as each of the symmetrical pairs are of similar steric bulk. Thus a cyclopentadienyl substituted at the 2 and the 5 positions with methyl and ethyl respectively, and substituted at the 3 and the 4 positions with hexyl and octyl, respectively, would be considered symmetric.

$(JR'_{z-2})$ is a heteroatom ligand in which J is an element with a coordination number of three from Group V A or an element with a coordination number of two from Group VI A of the Periodic Table of Elements, preferably nitrogen, phosphorus, oxygen or sulfur with nitrogen being preferred, and each R' is, independently a radical selected from a group consisting of $C_1$-$C_{20}$ hydrocarbyl radicals, substituted $C_1$-$C_{20}$ hydrocarbyl radicals wherein one or more hydrogen atoms is replaced by a halogen radical, an amido radical, a phosphido radical, an alkoxy radical or any other radical containing a Lewis acidic or basic functionality, and "z" is the coordination number of the element J;

each Q is, independently, any univalent anionic ligand such as a halide, hydride, or substituted or unsubstituted $C_1$-$C_{20}$ hydrocarbyl, alkoxide, aryloxide, amide, or phosphide, provided that where any Q is a hydrocarbyl such Q is not a cyclopentadienly or substituted cyclopentadienyl ligand, or both Q together may be an alkylidene or a cyclometallated hydrocarbyl or any other divalent anionic chelating ligand and provided when an ionic activator is used, Q is hydride, or a substituted or unsubstituted $C_1$-$C_{20}$ hydrocarbyl, or, alternatively, the transition metal compound is additionally contacted with an alkylating reagent such as an alumoxane or aluminum alkyl;

T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

and L is a neutral Lewis base such as diethylether, tetrahydrofuran, dimethylaniline, aniline, trimethylphosphine, n-butylamine, and the like; and "w" is a number from 0 to 3; L can also be a second transition metal compound of the same type such that the two metal centers M and M" are bridged by Q and Q", wherein M" has the same meaning as M and Q" has the same meaning as Q. Such compounds are represented by the formula:

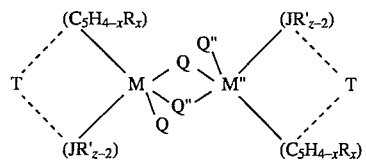

Examples of the T group which are suitable as a constituent group of the Group IV B transition metal component of the catalyst system are identified in column 1 of Table 1 under the heading "T".

Suitable, but not limiting, Group IV B transition metal compounds which may be utilized in the catalyst system of this invention include those wherein the T group bridge is a dialkyl, diaryl or alkylaryl silane, or methylene or ethylene. Exemplary of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Exemplary hydrocarbyl radicals for Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides of Q are dimethylamide, diethylamide, methylethylamide, di-t-butylamide, diisoproylamide and the like. Exemplary aryl amides are diphenylamide and any other substituted phenyl amides. Exemplary phosphides of Q are diphenylphosphide, dicyclohexylphosphide, diethylphosphide, dimethylphosphide and the like. Exemplary alkyldiene radicals for both Q together are methylidene, ethylidene and propylidene. Examples of the Q group which are suitable as a constituent group or element of the Group IV B transition metal component of the catalyst system are identified in column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals, amido-substituted hydrocarbon radicals, phosphido-substituted hydrocarbon radicals, alkoxy-substituted hydrocarbon radicals, and cyclopentadienyl rings containing one or more fused saturated or unsaturated rings. Suitable organometallic radicals, which may be substituted as an R group for at least one hydrogen atom in the cyclopentadienyl ring, include trimethylsilyl, triethylsilyl, ethyldimethylsilyl, methyldiethylsilyl, triphenylgermyl, trimethylgermyl and the like. Other suitable radicals that may be substituted for one or more hydrogen atom in the cyclopentadienyl ring include halogen radicals, amido radicals, phosphido radicals, alkoxy radicals, alkylborido radicals and the like. Examples of cyclopentadienyl ring groups $(C_5H_{4-x}R_x)$ which are suitable as a constituent group of the Group IV B transition metal component of the catalyst system are identified in Column 2 of Table 1 under the heading $(C_5H_{4-x}R_x)$.

Suitable hydrocarbyl and substituted hydrocarbyl radicals, which may be substituted as an R' group for at least one hydrogen atom in the heteroatom J ligand group, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radical, halogen radicals, amido radicals, phosphido radicals and the like. Examples of heteroatom ligand groups $(JR'_{z-2})$ which are suitable as a constituent group of the Group IV B transition metal component of the catalyst system are identified in column 3 of Table 1 under the heading $(JR'_{z-2})$.

Table 1 depicts representative constituent moieties for the "Group IV B transition metal component", the list is for illustrative purposes only and should not be construed to be limiting in any way. A number of final components may be formed by permuting all possible combinations of the constituent moieties with each other. Illustrative compounds are: dimethylsilyl(tetramethylcyclopentadienyl) (cyclohexylamido) zirconium dichloride, and dimethylsilyl(3,4-dimethylcyclopentadienyl) (cyclohexylamido) hafnium dichloride.

As noted, titanium species of the Group IV B transition metal compound have generally been found to yield catalyst systems which in comparison to their zirconium or hafnium analogous, are of higher activity and produce polymer of higher molecular weight. Illustrative, but not limiting of the titanium species which may exhibit such superior properties are; dimethylsilyl(tetramethylcyclopentadienyl) (t-butylamido) titanium dichloride, dimethylsilyl(3,4-di-t-butylcyclopentadienyl) (cyclododecylamido) titanium dichloride, dimethylsilyl(2,5-dimethylcyclopentadienyl) cyclododecylamido titanium dichloride, and dimethylsilyl(tetramethylcyclopentadienyl)(cyclododecylamido)titanium dichloride.

For illustrative purposes, the above compounds and those permuted from Table 1 include the neutral Lewis base ligand (L). The conditions under which complexes containing neutral Lewis base ligands such as ether or those which form dimeric compounds is determined by the steric bulk of the ligands about the metal center. For example, the t-butyl group in $Me_2Si(Me_4C_5)(N-t-Bu)ZrCl_2$ has greater steric requirements than the phenyl group in $Me_2Si(Me_4C_5)(NPh)ZrCl_2 \cdot Et_2O$ thereby not permitting ether coordination in the former compound. Similarly, due to the decreased steric bulk of the trimethylsilylcyclopentadienyl group in $[Me_2Si(Me_3SiC_5H_3)(N-t-Bu)ZrCl_2]_2$ versus that of the tetramethylcyclopentadienyl group in $Me_2Si(Me_4C_5)(N-t-Bu)ZrCl_2$, the former compound is dimeric and the latter is not.

To illustrate members of the Group IV B transition metal component, select any combination of the species in Table 1. An example of a bridged species would be dimethylsilylcyclopentadienyl (t-butylamido)dichloro zirconium.

TABLE 1

| T | $(C_5H_{(4-x)}R_x)$ | $(JR'_{x-2})$ | Q | M |
|---|---|---|---|---|
| dimethylsilyl | cyclopentadienyl | t-butylamido | hydride | |
| diethylsilyl | 3,4-dimethylcyclopentadienyl | phenylamido | methyl | zirconium |
| di-n-propylsilyl | 2,5-dimethylcyclopentadienyl | p-n-butylphenylamido | ethyl | hafnium |
| di-isopropylsilyl | 2-indenyl | cyclohexylamide | phenyl | titanium |
| di-n-butylsilyl | 3,4-diethylcyclopentadienyl | perflurophenylamide | n-propyl | L |
| di-t-butylsilyl | 2,5-diethylcyclopentadienyl | n-butylamide | isopropyl | ethylene |
| di-n-hexylsilyl | tetramethylcyclopentadienyl | methalamido | n-butyl | propylene |
| methylphenylsilyl | tetraethylcyclopentadienyl | ethylamido | amyl | 1-butene |
| ethylmethylsilyl | tetraphenylcyclopentadienyl | n-propylamido | isoseyl | 1,4-hexadiene |
| diphenylsilyl | tetra-n-propylcyclopentadienyl | isopropylamido | hexyl | 1,3-butadiene |
| di(p-butylphenethyl-silyl) | 3,4-di-n-butylcyclopentadienyl | benzylamido | isobutyl | 1,3-hexadiene |
| n-hexylmethylsilyl | 3,4-dicyclohexylcyclopentadienyl | cyclododecylamido | heptyl | acetylene |
| cyclopentamethylene-silyl | 2,5-di-n-butylcyclopentadienyl | n-butylamido | octyl | methylacetylene |
| cyclotetramethylenesilyl | 2,5-dicyclohexylcyclopentadienyl | t-butylphosphide | nonyl | benzyne |
| cyclotrimethylenesilyl | 3-n-octyl-4-n-hexylcyclopentadienyl | ethylphosphide | decyl | diethylether |
| dimethylgermanyl | 2-tetrahydroindenyl | phenylphosphido | cetyl | dimethylether |
| diethylgermanyl | 3-ethyl-4-n-propylcyclopentadienyl | cyclohexylphosphido | chloro | trimethylamine |
| phenylamido | 3-isopropyl-4-t-butylcyclopentadienyl | exo | fluoro | triphenylamine |
| t-butylamido | 3-phenyl-4-benzylcyclopentadienyl | sulfido | bromo | triethyamine |
| methylamido | 3,4-diphenylcyclopentadienyl | | iodo | triphenylphosphine |
| t-butylphosphido | 2,5-diphenylcyclopentadienyl | | methoxy | tetrahydrofuran |
| ethylphosphido | 3,4-bis(trimethylgermyl)cyclopentadienyl | | ethoxy | thiophene |
| phenylphosphido | 3,4-bis(trimethylstanny)cyclopentadienyl | | propoxy | dimethylsulfide |
| methylene | 3,4-bis(triethylplumbyl)cyclopentadienyl | | butoxy | |
| dimethylmethylene | 2-ethyl-5-n-propylcyclopentadienyl | | phenoxy | |
| diethylmethylene | 2-methyl-5-t-butylcyclopentadienyl | | dimethylamido | |
| ethylene | 2,5-bis(trifluromethyl)cyclopentadienyl | | diethylamido | |
| dimethylethylene | 3,4-bis(trimethylsilyl)cyclopentadienyl | | methylethylamido | |
| | 3,4-bis(N,N-dimethylamido)-cyclo- | | diphenylamido | |
| | | | diphenylphosphido | |

TABLE 1-continued

| T | $(C_5H_{(4-x)}R_x)$ | $(JR'_{x-2})$ | Q |
|---|---|---|---|
| dipropylethylene | pentadienyl | | dicyclohexylphosphido |
| propylene | 3,4-bis(dimethylphosphido)- | | dimethylphosphido |
| dimethylpropylene | cyclopentadienyl | | ethyleneglycol dianion |
| diethylpropylene | 3,4-dimethoxycyclopentadienyl | | (both Q) |
| 1,1-dimethyl-3,3-di- | 2,5-dimethoxycyclopentadienyl | | methylidene (both Q) |
| methylpropylene | 2,5-dimethyl-3,4-diethylcyclopentadienyl | | ethylidene (both Q) |
| tetramethyldisiloxane | 2,5-diethyl-3,4-dimethylcyclopentadienyl | | propylidene (both Q) |
| 1,1,4,4-tetramethyldisilyl ethylene | 2,5-dimethyl-3,4-di-t-butyl-cyclopentadienyl | | |

The Group IV B transition metal compounds can be prepared by reacting a cyclopentadienyl lithium compound with a dihalo compound, whereupon a lithium halide salt is liberated and a monohalo substituent is covalently bound to the cyclopentadienyl compound. The so substituted cyclopentadienyl reaction product is next reacted with a lithium salt of a phosphide, oxide, sulfide or amide (for the sake of illustrative purposes, a lithium amide) whereupon the halo element of the monohalo substituent group of the reaction product reacts to liberate a lithium halide salt and the amine moiety of the lithium amide salt is covalently bound to the substituent of the cyclopentadienyl reaction product. The resulting amine derivative of the cyclopentadienyl product is then reacted with an alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide.

The class of transition metal components preferred for use in the process for production of poly-α-olefins is that wherein the covalent bridging group T contains silicon and the heteroatom J of the heteroatom ligand is nitrogen. Accordingly, a preferred class of transition metal components are of the formula:

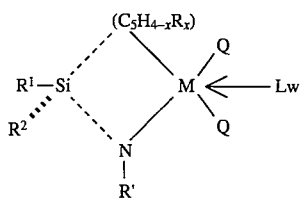

wherein Q, L, R', R, "x" and "w" are as previously defined and $R^1$ and $R^2$ are each independently a $C_1$ to $C_{20}$ hydrocarbyl radicals, substituted $C_1$ to $C_{20}$ hydrocarbyl radicals wherein one or more hydrogen atom is replaced by a halogen atom; $R^1$ and $R^2$ may also be joined forming a $C_3$ to $C_{20}$ ring which incorporates the silicon bridge.

The most preferred mono-cyclopentadienyl transition metal compounds which, according to the present invention, provide catalyst systems which are specific to the production of high molecular weight atactic poly-α-olefins include dimethylsilyl(tetramethylcyclopentadienyl)(cyclododecylamido) titanium dichloride, dimethylsilyl(tetramethylcyclopentadienyl)(cyclohexylamido) titanium dichloride, dimethylsilyl(tetramethylcyclopentadienyl)(exo-2-norbornylamido) titanium dichloride, dimethylsilyl(tetramethylcyclopentadienyl)(cyclododecylamido) titanium dimethyl, dimethylsilyl(tetramethylcyclopentadienyl)(cyclohexylamido) titanium dimethyl, and dimethylsilyl(tetramethylcyclopentadienyl)(exo-2-norbornylamido) titanium dimethyl.

THE ACTIVATOR/COCATALYST COMPONENT

An alumoxane may serve as the activator component of the catalyst system. Alumoxane is an oligomeric compound which may be represented by the general formula $(R^3\text{-Al-O})_m$ which is a cyclic compound, or may be $R^4(R^5\text{-Al-O})_m\text{-AlR}^6_2$ which is a linear compound. An alumoxane is generally a mixture of both the linear and cyclic compounds. In the general alumoxane formula $R^3$, $R^4$, $R^5$ and $R^6$ are, independently a $C_1$-$C_5$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide. Modified alumoxanes may also be used.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes which may be utilized in the catalyst systems of this invention are those prepared by the hydrolysis of a trialkylaluminum; such as trimethylaluminum, triethyaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Alumoxanes are well known in the art and methods for their production are illustrated by U.S. Pat. Nos. 4,542,199; 4,544,762; 5,015,749; and 5,041,585. A technique for preparing modified alumoxanes has been disclosed in U.S. Pat. No. 5,041,584, and in EPA 0 516 476 and in EP 0 561 476, all of which are incorporated herein by reference.

An ionic activator may serve as the metallocene cocatalyst. Generally these ionic activators comprise a cation which will irreversibly react with at least one ligand contained in the metallocene and a non-coordinating anion which is bulky, labile and stable. The cation reacts with the one metallocene ligand thereby generating an ion pair consisting of a metallocene cation and the non-coordinating anion. Other methods of generating the ion pair are known in the art and are suitable for use with the present invention.

The term "noncoordinating anion" means an anion which either does not coordinate to said cation or which is only weakly coordinated to said cation thereby remaining sufficiently labile to be displaced by a neutral Lewis base. "Compatible" noncoordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Noncoordinating anions useful in accordance with this invention are those which are compatible, stabilize the metallocene cation in the sense of balancing its ionic charge in a +1 state, yet retain sufficient lability to permit displacement by an ethylenically or acetylenically unsaturated monomer during polymerization. Additionally, the anions useful in this invention will be large or bulky in the sense of sufficient molecular size to largely inhibit or prevent neutralization of the metallocene cation by Lewis bases other than the polymerizable monomers that may be present in the polymerization process. Typically the anion will have a molecular size of greater than or equal to about 4 angstroms.

Descriptions of ionic catalysts for coordination polymerization comprised of metallocene cations activated by non-coordinating anions appear in the early work in EP-A-0 277 003, EP-A-0 277 004 and U.S. Pat. No. 5,198,401 and WO-A-92/00333. These teach a preferred method of preparation wherein metallocenes (bisCp and monoCp) are protonated by an anionic precursors such that an alkyl/hydride group is abstracted from a transition metal to make it both cationic and charge-balanced by the non-coordinating anion.

The use of ionizing ionic compounds not containing an active proton but capable of producing both the active metallocene cation and a noncoordinating anion is also known. See, EP-A-0 426 637 and EP-A- 0 573 403. An additional method of making the ionic catalysts uses ionizing anionic pre-cursors which are initially neutral Lewis acids but form the cation and anion upon ionizing reaction with the metallocene compounds, for example the use of tris(pentafluorophenyl) boron. See EP-A-0 520 732. Ionic catalysts for addition polymerization can also be prepared by oxidation of the metal centers of transition metal compounds by anionic pre-cursors containing metallic oxidizing groups along with the anion groups, see EP-A-0 495 375.

Where the metal ligands include halogen moieties (for example, bis-cyclopentadienyl zirconium dichloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-0 500 944 and EP-A1-0 570 982 for in situ processes describing the reaction of alkyl aluminum compounds with dihalo-substituted metallocene compounds prior to or with the addition of activating anionic compounds.

The catalyst system of this invention may be supported on an inert carrier. Methods of supporting alumoxane activated metallocene catalyst systems are well known in the art. Methods of supporting ionic catalysts comprising metallocene cations and noncoordinating anions are described in U.S. Pat. No. 5,057,475, WO91/09882, WO 94/03506 and in co-pending U.S. Ser. No. 08/248,284, filed Aug. 3 1994. The methods generally comprise either physical adsorption on traditional polymeric or inorganic supports that have been largely dehydrated and dehydroxylated, or using neutral anion precursors that are sufficiently strong Lewis acids to activate retained hydroxy groups in silica containing inorganic oxide supports such that the Lewis acid becomes covalently bound and the hydrogen of the hydroxy group is available to protonate the metallocene compounds.

Catalyst Systems

The catalyst systems employed in the method of the invention comprise a complex formed upon admixture of the Group IV B transition metal component with one or more activator components. The catalyst system may be prepared by addition of the requisite Group IV B transition metal and activator components to an inert solvent in which olefin polymerization can be carried out by a solution, slurry, gas phase or bulk phase polymerization procedure.

The catalyst system may be conveniently prepared by placing the selected Group IV B transition metal component and the selected activator component, in any order of addition, in an alkane or aromatic hydrocarbon solvent—preferably one which is also suitable for service as a polymerization diluent. When the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. If desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

In accordance with this invention optimum results are generally obtained wherein the Group IV B transition metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1 or the ionic activator component is present in an amount to provide a molar activator to transition metal molar ratio of from about 50:1 to about 1:20. Sufficient solvent should be employed so as to provide adequate heat transfer away from the catalyst components during reaction and to permit good mixing.

The catalyst system ingredients—that is, the Group IV B transition metal, the activator component, and polymerization diluent—can be added to the reaction vessel rapidly or slowly. The temperature maintained during the contact of the catalyst components can vary widely, such as, for example, from −100° to 300° C. Greater or lesser temperatures can also be employed. Preferably, during formation of the catalyst system, the reaction is maintained within a temperature of from about 25° to 100° C., most preferably about 25° C.

At all times, the individual catalyst system components, as well as the catalyst system once formed, are protected from oxygen and moisture. Therefore, the reactions to prepare the catalyst system are performed in an oxygen and moisture free atmosphere and, where the catalyst system is recovered separately it is recovered in an oxygen and moisture free atmosphere. Preferably, therefore, the reactions are performed in the presence of an inert dry gas such as, for example, helium or nitrogen.

Polymerization Process

In a preferred embodiment of the process of this invention the catalyst system is utilized in the liquid phase (slurry, solution, suspension or bulk phase or combination thereof), high pressure fluid phase or gas phase polymerization of an α-olefin monomer. These processes may be employed singularly or in series. The liquid phase process comprises the steps of contacting an α-olefin monomer with the catalyst system in a suitable polymerization diluent and reacting said monomer in the presence of said catalyst system for a time and at a temperature sufficient to produce an amorphous poly-α-olefin as desired.

The monomer for such process comprises an α-olefin having 3 to 20 carbon atoms. Propylene is a preferred monomer. Homopolymers of higher α-olefin such as 1-butene, styrene, and copolymers of propylene and/or $C_4$ or higher α-olefins, diolefins, cyclic olefins and internal olefins can also be prepared. Conditions most preferred for the homo- or copolymerization of the α-olefin are those wherein an α-olefin is submitted to the reaction zone at pressures of from about 0.019 psia to about 50,000 psia, preferably 50 to 1500 psia, more preferably 120 to 1000 psia, and the reaction temperature is maintained at from about −100° to about 300° C., preferably 20° C. to 180° C., most preferably 30° C. to 120° C. The aluminum to transition metal molar ratio is preferably from about 1:1 to 20,000:1 or the ionic activator to transition metal molar ratio is from abut 50:1 to about 1:20.

A more preferable range for the aluminum to transition metal molar ratio would be 1:1 to 2000:1 and for an ionic activator to transition metal molar ratio would be about 20:1 to about 1:5. The reaction time is preferably from about 10 seconds to about 10 hours.

Scavengers may be used as described in U.S. Ser. No. 07/957,305 incorporated herein by reference Without limiting in any way the scope of the invention, one means for carrying out the process of the present invention for production of a copolymer is as follows: in a stirred-tank reactor liquid α-olefin monomer is introduced, such as propylene. The catalyst system is introduced via nozzles in either the vapor or liquid phase. The reactor contains a liquid phase composed substantially of the liquid α-olefin monomer together with a vapor phase containing vapors of the monomer. The reactor temperature and pressure may be controlled via reflux of vaporizing α-olefin monomer (autorefrigeration), as well as by cooling coils, jackets etc. The polymerization rate is controlled by the concentration of catalyst.

By appropriate selection of (1) Group IV B transition metal component for use in the catalyst system; (2) the type and amount of activator used; (3) the polymerization diluent type and volume; (4) reaction temperature; and (5) reaction pressure, one may tailor the product polymer to the weight average molecular weight value desired while still maintaining the molecular weight distribution to a value below about 4.0, preferably below 3.5, more preferably from about 4.0 to about 1.5, even more preferably from about 3.5 to about 1.5. and even more preferably from about 3.3 to about 1.5.

When higher molecular weight amorphous polypropylene is desired the catalyst is titanium based and the polymer preferably has a molecular weight of greater than about 200,000, or from about 200,000 to 2,000,000; preferably greater than about 500,000 or from about 500,000 to about 2,000,000. Preferred polymers exhibit either no appreciable melting point or a melting point of less than about 2 J/g, more preferably less than about 0.1 J/g and even more preferably less than about 0.6 J/g. The Bernoullianity index of such polymers (B) is defined as $B = 4[mm][rr]/[mr]^2$. Preferably B is about 1.3±about 0.6.

In addition, preferred polymers have a higher percentage of racemic dyads (r) than meso dyads (m). The preferred polymers also have $\%(CH_2)_2$ sequences of 3 to 30. Those metallocenes of the catalyst systems which give lower $\%(CH_2)_2$ sequence values (3–6) tend to have R' bonded to J via a 3° carbon atom whereas those which give higher $\%(CH_2)_2$ sequence values (8–20), tend to have a R' bonded to J via a 2° carbon atom.

The preferred polymerization diluents for practice of the process of the invention are aromatic diluents, such as toluene, or alkanes, such as hexane. Optionally, the α-olefin itself may be used as the solvent.

The resins that are prepared in accordance with this invention can be used to make a variety of products including films and fibers, adhesives, compatibilizers and the like.

EXAMPLES

In the examples which illustrate the practice of the invention the analytical techniques described below were employed for the analysis of the resulting polyolefin products. Molecular weight determinations for the polyolefin products of examples 1, 2, and 3 were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used.

Molecular weight determinations for the polyolefin products of examples 4–17 were made by Gel Permeation Chromatography according to the following technique. Molecular weights (MW=weight average molecular weight; Mn=number average molecular weight) and molecular weight distributions (Mw/Mn=MWD) were measured using a Waters 150-C gel permeation chromatograph equipped with a differential refractive with 1,2,4-trichlorobenzene as the mobile phase. Three (Showa Denko America, Inc.) mixed bed columns (AT- 80M/S) were used in series.

These techniques are discussed in "Liquid Chromatography of Polymers and Related Materials III", J. Cazes editor, Marcel Dekker. 1981, p. 207, which is incorporated herein by reference. No corrections for column spreading were employed. A precision of 0.1 units was demonstrated for Mw/Mn which was calculated from elution times.

The numerical analyses for examples 1–3 were performed using the commercially available Beckman/CIS customized LALLS software in conjunction with the standard Gel Permeation package, run on a HP 1000 computer. The numerical analyses for examples 3–18 were performed using Waters Expert Ease software package.

Polymer samples for $^{13}$C NMR spectroscopy were dissolved in $d_2$-1,1,2,2-tetrachloroethane and the samples were recorded at 125° C. using a NMR spectrometer of 75 or 100 MHz. Polymer resonance peaks are referenced to mmmm= 21.8 ppm. Calculations involved in the characterization of polymers by NMR follow the work of F. A. Bovey in "Polymer Conformation and Configuration" Academic Press, New York 1969 and J. Randall in "Polymer Sequence Determination, Carbon-13 NMR Method, Academic Press, New York, 1977. The Bernoullianity index (B) is defined as B= 4[mm][rr]/[mr]$^2$. The percent of methylene sequences of two in length, %(CH$_2$)$_2$, were calculated as follows: the integral of the methyl carbons between 14–18 ppm (which are equivalent in concentration to the number of methylenes in sequences of two in length) divided by the sum of the integral of the methylene sequences of one in length between 45–49 ppm and the integral of the methyl carbons between 14–18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Tensile, elongation, yield stress and modulus were measured according to ASTM D 412 on an Instron Tensile Tester. Percent elastic recovery was determined according to the following equation: % recovery= [(2Lo-L')/Lo]×100; wherein Lo is the original length of the sample, L' is the length of the sample after being held at 200% elongation for 10 minutes and then released and allowed to relax for 10 minutes at room temperature. Intrinsic viscosity (I.V.) was measured in decalin at 135° C. using ASTM Procedure D1601-86 using a Schott AVS/G or AVS/PA viscometer.

The melting temperature (Tm, second melt) of the polymer was measured by using Dupont Instruments 912 differential scanning calorimeter (DSC) which is equipped with the standard numerical analysis software. The area under the melting peak represents the enthalpy of melt and is reported in Joules per gram (J/g). Standard procedure involved equilibrating the sample at 0° C., increasing the temperature at a rate of 10° C./min. to 200° C. (first melt); remaining at 200° C. for 2 minutes; decreasing the temperature at a rate of 10° C./min. to 0° C. (crystallization temperature); remaining at 0° C. for 2 minutes; and increasing the temperature at a rate of 10° C./min. to 200° C. (second melt). Typical crystallization and second melt plots were recorded between 0° C. and 180° C.

The following examples are intended to illustrate specific embodiments of the invention and are not intended to limit the scope of the invention.

EXAMPLES PRODUCING AMORPHOUS POLY-α-OLEFIN

All procedures were performed under an inert atmosphere of helium or nitrogen. Solvent choices were often optional, for example, in most cases either pentane or 30–60 petroleum ether could be interchanged. The choice between tetrahydrofuran (thf) and diethyl ether (ether) is a bit more restricted, but in several reactions, either could be used. The lithiated amides were prepared from the corresponding amines and either n-BuLi or MeLi. Published methods for preparing LiHC$_5$Me$_4$ include C. M. Fendrick et al., *Organometallics* 1984, 3, 819 and F. H. Kohler and K. H. Doll, *Z. Naturforsch* 1982, 376, 144. Other lithiated substituted cyclopentadienyl compounds are typically prepared from the corresponding cyclopentadienyl ligand and n-BuLi or MeLi, or by reaction of MeLi with the proper fulvene. TiCl$_4$ was typically used in its etherate form. The etherate can be prepared by simply adding TiCl$_4$ to ether and filtering off the solid product which is then vacuum dried. TiCl$_4$, ZrCl$_4$, HfCl$_4$, amines, silanes, substituted and unsubstituted cyclopentadienyl compounds or precursors, and lithium reagents were purchases from Aldrich Chemical Company, Petrarch Systems or Cerac. Methylalumoxane was supplied by Ethyl Corporation (now Albemarle). Triethylaluminum (TEAL) was purchased as a 25 wt % solution in heptane from Akzo. [DMAH][(B(pfp)$_4$] (DMAH= dimethylanalinium; pfp=perfluorophenyl) was prepared as described in EPA 277004 and EP 277003.

EXAMPLE A

Compound A:

Part 1. LiHC$_5$Me$_4$ (10.0 g, 0.078 mol) was slowly added to a Me$_2$SiCl$_2$ (11.5 ml, 0.095 mol, in 225 ml of tetrahydrofuran solution). The solution was stirred for 1 hour to insure a complete reaction. The solvent was then removed in vacuo. Pentane was added to precipitate the LiCl which was filtered off. The solvent was then removed from the filtrate leaving behind the pale yellow liquid, (C$_5$Me$_4$H)SiMe$_2$Cl (15.34 g, 0.071 mol).

Part 2. (C$_5$Me$_4$H)SiMe$_2$Cl (10.0 g, 0. 047 mol) was slowly added to a suspension of LiHN-t-Bu (3.68 g, 0.047 mol, approximately 100 ml of thf). The mixture was stirred overnight. The thf was then removed in vacuo. Petroleum ether (approximately 100 ml) was added to precipitate the LiCl which was filtered off. The solvent was removed from the filtrate leaving behind the pale yellow liquid, Me$_2$Si(C$_5$Me$_4$H) (HN-t-Bu) (11.4 g, 0.044 mol).

Part 3. Me$_2$Si(C$_5$Me$_4$H) (HN-t-Bu) (11.14 g, 0.044 mol) was diluted with approximately 100 ml of ether. MeLi (1.4M, 64 ml, 0.090 mol) was slowly added. The mixture was allowed to stir for ½ hour after the final addition of MeLi. The ether was reduced in volume prior to filtering off the product. The product, Li$_2$ [Me$_2$Si (C$_5$Me$_4$) (N-t-Bu)], was washed with several small portions of ether, then vacuum dried.

Part 4. Li$_2$[Me$_2$Si(C$_5$Me$_4$) (N-t-Bu)] (3.0 g, 0.011 mol) was suspended in approximately 150 ml of ether. ZrCl$_4$ (2.65 g, 0.011 mol) was slowly added and the resulting mixture was allowed to stir overnight. The ether was removed in vacuo. Pentane was added to precipitate the LiCl which was filtered off. The pentane was significantly reduced in volume and the pale yellow solid was filtered off and washed with solvent. Me$_2$Si(C$_5$Me$_4$)(N-t-Bu)ZrCl$_2$ (1.07 g, 0.0026 mole) was recovered. Additional Me$_2$Si(C$_5$Me$_4$)(N-t-Bu)ZrCl$_2$ was recovered from the filtrate by repeating the recrystallization procedure. Total yield: 1.94 g, 0.0047 mol.

EXAMPLE B

Compound B:

Part 1. (C$_5$Me$_4$H)SiMe$_2$Cl was prepared as described in Example A for the preparation of compound A, Part 1.

Part 2. (C$_5$Me$_4$H)SiMe$_2$Cl (8.0 g, 0.037 mol) was slowly added to a suspension of LiHNC$_{12}$H$_{23}$(C$_{12}$H$_{23}$= cyclododecyl, 7.0 g, 0.037 mol, approximately 80 ml thf). The mixture was stirred overnight. The thf was then removed via a vacuum to a cold trap held at −196° C. Petroleum ether and toluene were added to precipitate the LiCl. The mixture was filtered through Celite. The solvent was removed from the filtrate. $Me_2Si(C_5Me_4H)(NHC_{12}H_{23})$ (11.8 g, 0.033 mol) was isolated as a pale yellow liquid.

Part 3. $Me_2Si(C_5Me_4H)(NHC_{12}H_{23})$ (11.9 g, 0.033 mol) was diluted with approximately 150 ml of ether. MeLi (1.4M, 47 ml, 0.066 mol) was slowly added. The mixture was allowed to stir for 2 hours after the final addition of MeLi. The ether was reduced in volume prior to filtering off the product. the product, $[Me_2Si(C_5Me_4H)(NC_{12}H_{23})]Li_2$ (3.0 g, 0.008 mol) was washed with several small portions of ether, then vacuum dried to yield 11.1 g (0.030 mol) of product.

Part 4. $[Me_2Si(C_5Me_4H) (NC_{12}H_{23})]Li_2$ (3.0 g, 0.008 mol) was suspended in cold ether. $TiCl_4 \cdot 2Et_2O$ (2.7 g, 0.008 mol) was slowly added and the resulting mixture was allowed to stir overnight. The ether was removed via a vacuum to a cold trap held at −196° C. Methylene chloride was added to precipitate the LiCl. The mixture was filtered through Celite. The solvent was significantly reduced in volume and petroleum ether was added to precipitate out the product. This mixture was refrigerated prior to filtration in order to maximize precipitation. The solid collected was recrystallized from methylene chloride and $Me_2Si(C_5Me_4)(NC_{12}H_{23})TiCl_2$ was isolated (1.0 g, 2.1 mmol).

EXAMPLE D

Compound D:

Part 1. $(C_5Me_4H)SiMe_2Cl$ was prepared as described in Example A for the preparation of compound A, Part 1.

Part 2. $(C_5Me_4H)SiMe_2Cl$ (6.0 g, 0.028 mol) was diluted in ~100 ml THF. $LiHN-C_7H_{11}$ (lithiated exonorbornylamine, 3.26 g, 0.028 mol) was added and the reaction mixture was allowed to stir for 3 hours. The solvent was removed via vacuum, and ~100 ml of diethyl ether was added. To this mixture which was chilled to −30° C., 36 ml of MeLi (~1.4M in ether, 0.050 mol, assumes a 90% yield in the previous step) was added and the reaction mixture was stirred for 2 hours. The mixture was cooled to −30° C. and $TiCl_4 \cdot 2Et_2O$ (8.15 g, 0.024 mol, assumes a 95% yield in the previous step) was slowly added and the reaction mixture was allowed to stir overnight. The solvent was removed via vacuum and pentane was added. This mixture was filtered through Celite to remove the LiCl. The filtrate was reduced in volume and cooled to −30° C. to induce precipitation of the product. The product was filtered off and washed with cold pentane yielding 1.3 g (3.2 mmol) of the yellow solid, $Me_2Si(Me_4C_5)(N-C_7H_{11})TiCl_2$.

EXAMPLE E

Compound E:

Part 1. $Li_2[Me_2Si(C_5Me_4)(N-t-Bu)]$ was prepared as described in example A, Part 3.

Part 2. $Li_2[Me_2Si(C_5Me_4)(N-t-Bu)]$ (6.6 g, 0.025 mol) was suspended in cold ether. $TiCl_4 \cdot 2Et_2O$ (8.4 g, 0.025 mol) was slowly added and the resulting mixture was allowed to stir overnight. The ether was removed via a vacuum to a cold trap held at −196° C. Methylene chloride was added to precipitate out the LiCl. The mixture was filtered through Celite. The solvent was significantly reduced in volume and petroleum ether was added to precipitate the product. This mixture was refrigerated prior to filtration in order to maximize precipitation. $Me_2Si(C_5Me_4)(N-t-Bu)TiCl_2$ was isolated (2.1 g, 5.7 mmol).

EXAMPLE F

Compound F:

Part 1. $Me_2Si(C_5Me_4)(NC_{12}H_{23})TiCl_2$ was prepared as in Example B, Part 4.

Part 2. $Me_2Si(C_5Me_4)(NC_{12}H_{23})TiMe_2$ was prepared by adding a stoichiometric amount of MeLi (1.4M in ether) to $Me_2Si(C_5Me_4)(NC_{12}H_{23})TiCl_2$ suspended in ether. The white solid recrystallized from toluene and petroleum ether was isolated in a 57% yield.

Polymerization Examples

Polymerization Example 1

The polymerization run was performed in a 1-liter autoclave reactor equipped with a paddle stirrer, an external water jacket for temperature control, a regulated supply of dry nitrogen, ethylene, propylene, and hexane, and a septum inlet for the introduction of other solvents or comonomers, transition metal compound and alumoxane solutions. The reactor was dried and degassed thoroughly prior to use. A typical run consisted of adding 100 ml of toluene, 400 ml of propylene, 7 ml of 1.0M MAO, and 6.9 mg of preactivated compound A (6 ml of a 11.5 mg of compound A plus 0.5 ml of 1.0M MAO in 9.5 ml of toluene solution) into the reactor heated at 50° C. The polymerization reaction was limited to 30 minutes. The reaction was ceased by rapidly cooling and venting the system and the catalyst was killed by thoroughly exposing the product to air. The solvent was evaporated off of the polymer by a stream of nitrogen. Atactic polypropylene was recovered (2.9 g, MW=5100, MWD=1.86, mmmm=0.086, mmmr=0.142, rmmr=0.072, mmrr=0.130, mmrm+rmrr=0.251, mrmr=0.118, rrrr= 0.049, rrrm=0.094, mrrm=0.059, m=0.548, r= 0.452, B=0.97).

Polymerization Example 2

Using the same reactor design and general procedure already described, 500 ml of propylene, 1 ml of 1.0M MAO, and 1.0 mg of compound B in 1.0 ml of 1.0M MAO were added to the reactor heated at 60° C. The reaction was allowed to run for 2 hours, followed by rapidly cooling and venting the system. The catalyst was killed by thoroughly exposing the product to air. After evaporation of the excess propylene, 113 g of atactic polypropylene was recovered (MW=723,700, MWD =1.85, mmmm=0.034, mmmr=0.089, rmmr=0.056, mmrr =0.105, mmrm+rmrr=0.251, mrmr= 0.152, rrrr= 0.074, rrrm=0.146, mrrm=0.094, m=0.432, r= 0.568, B=0.87). The polymer exhibited a melting point at 129° C. (0.31 J/g).

Polymerization Example 3

Using the same reactor design and general procedure already described, 400 ml of propylene, 2 ml of 1.0M MAO, and 1.0 mg of compound B in 1.0 ml of 1.0M MAO were added to the reactor heated at 40° C. The reaction was allowed to run for 1 hour, followed by rapidly cooling and venting the system. The catalyst was killed by thoroughly exposing the product to air. After evaporation of the excess propylene, 126 g of atactic polypropylene was recovered (MW=1,255,000, MWD=1.90, mmmm=0.040, mmmr= 0.090, rmmr=0.060, mmrr=0.110, mmrm+rmrr=0.250, mrmr=0.150, rrrr= 0.070, rrrm=0.140, mrrm=0.090, m=0.445, r= 0.555, B=0.88).

Polymerization Example 4

Using the same reactor design and general procedure already described, 400 ml of propylene, 2 ml of 1.0M MAO, and 1.0 mg of compound B in 1.0 ml of 1.0M MAO were added to the reactor heated at 40° C. The reaction was allowed to run for 1 hour, followed by rapidly cooling and venting the system. The catalyst was killed by thoroughly exposing the product to air. After evaporation of the excess propylene, 66.4 g of atactic polypropylene was recovered (MW=1,318,700, MWD=1.96, I.V.=10.26 dl/g, %(CH$_2$)$_2$= 10.6, mmmm= 0.040, mmmr=0.102, rmmr=0.067, mmrr= 0.111, mmrm+rmrr=0.246, mrmr=0.125, mm=0.082, rrrm= 0.142, mrrm=0.085, m=0.449, r=0.551, B=1.11). The polymer did not exhibit a melting point.

Polymerization Example 5

Using the same reactor design and general procedure already described, 400 ml of propylene, 2 ml of 1.0M MAO, and 1 ml of a compound B solution (13.4 mg of compound B in 10 ml of toluene) were added to the reactor heated at 40° C. The reaction was allowed to run for 15 minutes, followed by rapidly cooling and venting the system. The catalyst was killed by thoroughly exposing the product to air. After evaporation of the excess propylene, 64.9 g of atactic polypropylene was recovered (MW=1,824,100, MWD= 1.77, I.V.=19.28 dl/g, mmmm=0.037, mmmr=0.085, rmmr= 0.066, mmrr= 0.102, mmrm+rmrr=0.248, mrmr=0.160, rrrr= 0.062, rrrm=0.156, mrrm=0.084, m=0.443, r=0.557, B= 0.87, tensile @50° C.=220 psi, tensile @75° C.=120 psi, tensile @90° C.—sample broke, elongation @50° C.=1500%, elongation @75° C.=350%, elongation @90° C.—sample broke, modulus @50° C.=250 psi, modulus @75° C.—not determined, modulus @90—sample broke, elastic recovery @25° C.=97%, elastic recovery @50° C. and @75° C.—not determined, elastic recovery @90° C.—sample broke). The polymer did not exhibit a melting point.

Polymerization Example 6

Using the same reactor design and general procedure already described, 350 ml of propylene, 0.2 ml of 1.0M MAO, and 3.0 mg of compound B in 3.0 ml of 1.0M MAO were added to the reactor heated at 70° C. The reaction was allowed to run for 1 hour, followed by rapidly cooling and venting the system. The catalyst was killed by thoroughly exposing the product to air. After evaporation of the excess propylene, 58.0 g of atactic polypropylene was recovered (MW=693,200, MWD =1.95, %(CH$_2$)$_2$=12.1, mmmm= 0.029, mmmr=0.079, rmmr=0.060, mmrr=0.105, mmrm+ rmrr=0.255, mrmr= 0.149, rrrr=0.076, rrrm=0.155, mrrm= 0.091, m= 0.423, r=0.577, B=0.83). The polymer exhibited a melting point at 123° C. (0.29 J/g).

Polymerization Example 8

Using the same reactor design and general procedure already described, 400 ml of propylene, 2 ml of 1.0M MAO, and 0.85 mg of compound D in 1.0 ml of 1.0M MAO were added to the reactor heated at 40° C. The reaction was allowed to run for 1 hour, followed by rapidly cooling and venting the system. The catalyst was killed by thoroughly exposing the product to air. After evaporation of the excess propylene, 15.0 g of atactic polypropylene was recovered (MW=391,000, MWD =1.80, I.V.=3.63 dl/g, %(CH$_2$)$_2$= 16.3, mmmm=0.020, mmmr=0.051, rmmr=0.060, mmrr= 0.093, mmrm+rmrr= 0.232, mrmr=0.104, rrrr=0.167, rrrm= 0.190, mrrm= 0.082, m=0.346, r=0.654, B=1.26). The polymer exhibited a melting point at 123° C. (0.08 J/g).

Polymerization Example 9

Using the same reactor design and general procedure already described, 400 ml of propylene, 2 ml of 1.0M MAO, and 1.0 ml of a compound D solution (8.5 mg of compound D in 10 ml of 1.0M MAO) were added to the reactor heated at 40° C. The reaction was allowed to run for 30 minutes, followed by rapidly cooling and venting the system. The catalyst was killed by thoroughly exposing the product to air. After evaporation of the excess propylene, 23.0 g of atactic polypropylene was recovered (MW=229,500, MWD=1.81, I.V.=2.26 dl/g, %(CH$_2$)$_2$=15.7, mmmm=0.020, mmmr= 0.048, rmmr=0.057, mmrr=0.105, mmrm+rmrr=0.226, mrmr=0.130, rrrr=0.156, rrrm=0.182, mrrm=0.076, m=0.356, r=0.644, B=0.98). The polymer exhibited a melting point at 122° C. (0.55 J/g).

Polymerization Example 10

Using the same reactor design and general procedure already described, 400 ml of propylene, 2 ml of 1.0M MAO, and 1.15 mg of a compound D in 1.0 ml of 1.0M MAO were added to the reactor heated at 40° C. The reaction was allowed to run for 15 minutes, followed by rapidly cooling and venting the system. The catalyst was killed by thoroughly exposing the product to air. After evaporation of the excess propylene, 11.2 g of atactic polypropylene was recovered (MW=520,900, MWD=2.45, % (CH$_2$)$_2$=13.7, mmmm=0.075, mmmr=0.056, rmmr=0.056, mmrr=0.123, mmrm + rmrr=0.212, mrmr= 0.107, rrrr=0.157, rrrm= 0.159, mrrm=0.055, m=0.408, r=0.592, B=1.42).

Polymerization Example 11

Using the same reactor design and general procedure already described, 400 ml of propylene, 2 ml of 1.0M MAO, and 0.85 mg of a compound D in 1.0 ml of 1.0M MAO were added to the reactor heated at 20° C. The reaction was allowed to run for 1 hour, followed by rapidly cooling and venting the system. The catalyst was killed by thoroughly exposing the product to air. After evaporation of the excess propylene, 2.0 g of atactic polypropylene was recovered (MW=197,700, MWD =1.91, mmmm=0.022, mmmr=0.048, rmmr=0.055, mmrr =0.106, mmrm+rmrr=0.227, mrmr= 0.132, rrrr= 0.150, rrrm=0.180, mrrm=0.082, m=0.356, r= 0.644, B=0.95).

Polymerization Example 12

Using the same reactor design and general procedure already described, 400 ml of propylene, 2 ml of 1.0M MAO, and 0.77 mg of a compound E in 1.0 ml of 1.0M MAO were added to the reactor heated at 40° C. The reaction was allowed to run for 1 hour, followed by rapidly cooling and venting the system. The catalyst was killed by thoroughly exposing the product to air. After evaporation of the excess propylene, 3.5 g of atactic polypropylene was recovered (MW=355,400, MWD =1.74, I.V.=3.59 dl/g, %(CH$_2$)$_2$=3.8, mmmm=0.012, mmmr=0.040, rmmr=0.051, mmrr=0.103, mmrm + rmrr= 0.199, mrmr=0.086, rrrr=0.262, rrrm=0.194, mrrm= 0.055, m=0.297, r=0.703, B=1.40). The polymer exhibited a melting point at 122° C. (0.31 J/g).

Polymerization Example 13

Using the same reactor design and general procedure already described, 400 ml of propylene, 0.4 ml of 25 wt % TEAL in heptane, and 4 ml of preactivated compound F (100 mg of compound F premixed with 50 mg of [DMAH] [B(pfp)$_4$] in 5 ml of toluene) were added to the reactor heated at 40° C. The reaction was allowed to run for 30 minutes, followed by rapidly cooling and venting the system. The catalyst was killed by thoroughly exposing the product to air. After evaporation of the excess propylene, 30.0 g of atactic polypropylene was recovered (MW=308, 200, MWD=3.27, %(CH$_2$)$_2$=14.9, mmmm=0.027, mmmr= 0.082, rmmr= 0.055, mmrr=0.110, mmrm+rmrr=0.247, mrmr=0.142, rrrr=0.077, rrrm=0.158, mrrm=0.103, m=0.413, r =0.587, B=0.89). The polymer exhibited a melting point at 122° C. (0.22 J/g).

Polymerization Example 14

Using the same reactor design and general procedure already described, 400 ml of propylene, 0.4 ml of 25 wt % TEAL in heptane, and 4 ml of preactivated compound F (100 mg of compound F premixed with 50 mg of [DMAH]

[B(pfp)$_4$] in 5 ml of toluene) were added to the reactor heated at 40° C. The reaction was allowed to run for 30 minutes, followed by rapidly cooling and venting the system. The catalyst was killed by thoroughly exposing the product to air. After evaporation of the excess propylene, 32.7 g of atactic polypropylene was recovered (MW=359,300, MWD=3.05, I.V.=3.29 dl/g, %(CH$_2$)$_2$=15.0, mmmm= 0.027, mmmr= 0.078, rmmr=0.056, mmrr=0.107, mmrm+ rmrr=0.254, mrmr=0.134, rrrr=0.083, rrrm=0.164, mrrm= 0.097, m=0.408, r=0.592, B=0.90). The polymer exhibited a melting point at 123° C. (0.24 J/g).

Polymerization Example 15

Using the same reactor design and general procedure already described, 400 ml of propylene, 0.4 ml of 25 wt % TEAL in heptane, and 1 ml of preactivated compound F (100 mg of compound F premixed with 50 mg of [DMAH][B(pfp)$_4$] in 5 ml of toluene) were added to the reactor heated at 40° C. The reaction was allowed to run for 30 minutes, followed by rapidly cooling and venting the system. The catalyst was killed by thoroughly exposing the product to air. After evaporation of the excess propylene, 4.6 g of atactic polypropylene was recovered (MW=167,800, MWD=1.81, %(CH$_2$)$_2$=13.6, mmmm=0.028, mmmr=0.079, rmmr= 0.059, mmrr=0.107, mmrm+rmrr=0.251, mrmr= 0.139, rrrr=0.077, rrrm=0.159, mrrm=0.101, m=0.414, r =0.586, B=0.91). The polymer did not exhibit a melting point.

Polymerization Example 16

Using the same reactor design and general procedure already described, 400 ml of propylene, 0.4 ml of 25 wt % TEAL in heptane, and 2 ml of preactivated compound F (100 mg of compound F premixed with 50 mg of [DMAH][B(pfp)$_4$] in 5 ml of toluene) were added to the reactor heated at 40° C. The reaction was allowed to run for 30 minutes, followed by rapidly cooling and venting the system. The catalyst was killed by thoroughly exposing the product to air. After evaporation of the excess propylene, 10.0 g of atactic polypropylene was recovered (MW=115,400, MWD=1.67, I.V.=1.27 dl/g, %(CH$_2$)$_2$=14.2, mmmm= 0.030, mmmr= 0.074, rmmr=0.050, mmrr=0.108, mmrm+ rmrr=0.249, mrmr=0.144, rrrr=0.074, rrrm=0.158, mrrm= 0.115, m=0.403, r=0.597, B=0.85).

Polymerization Example 17

Using the same reactor design and general procedure already described, 400 ml of propylene, and 2 ml of preactivated compound F (20 mg of compound F premixed with 10 mg of [DMAH][B(pfp)$_4$] in 2 ml of toluene) were added to the reactor heated at 50° C. An immediate temperature rise of 22° C. occurred and the polymerization was allowed to proceed for only 1 minute, followed by rapidly cooling and venting the system. The catalyst was killed by thoroughly exposing the product to air. After evaporation of the excess propylene, 11 g of atactic polypropylene was recovered (MW=838,700, MWD=2.30).

The characterization Data for Examples 1–17 are presented in Tables 2–4. The data show that these products are amorphous, of high molecular weight and of narrow molecular weight distribution. With respect to the whole of the present invention, by appropriate selection of (1) Group IVB transition metal component for use in the catalyst system; (2) the type and amount of cocatalyst or activator used; (3) the polymerization diluent type and volume; and (4) reaction temperature, one may tailor the product polymer to the weight average molecular weight value desired and to the tacticity desired while still maintaining the molecular weight distribution at a value below about 6.0, preferably below 4.0, more preferably below 3.5.

The resins that are prepared in accordance with this invention can be used to make a variety of products including films, fibers, adhesives, compatibilizers and molded articles.

The invention has been described with reference to its preferred embodiments. Those of ordinary skill in the art may, upon reading this disclosure, appreciate changes or modifications which do not depart from the scope and spirit of the invention as described above or claimed hereafter.

TABLE 2

| Ex # | TMC | TMC (mg) | molar Al/M | molar Act/M | C$_3$ (ml) | T (C.) | Time (hr) | Polymer yield (g) |
|---|---|---|---|---|---|---|---|---|
| 1 | A | 6.90 | 435 | — | 400 | 50 | 0.5 | 2.9 |
| 2 | B | 1.00 | 957 | — | 500 | 60 | 2 | 112.8 |
| 3 | B | 1.00 | 1435 | — | 400 | 40 | 1 | 125.7 |
| 4 | B | 1.00 | 1435 | — | 400 | 40 | 1 | 66.4 |
| 5 | B | 1.34 | 714 | — | 400 | 40 | 0.3 | 64.9 |
| 6 | B | 3.00 | 510 | — | 350 | 70 | 1 | 58.0 |
| 7 | D | 0.85 | 1434 | — | 400 | 40 | 1 | 15.0 |
| 8 | D | 0.85 | 1434 | — | 400 | 40 | 0.5 | 23.0 |
| 9 | D | 1.15 | 1060 | — | 400 | 40 | 0.3 | 11.2 |
| 10 | D | 0.85 | 1434 | — | 400 | 20 | 1 | 2.0 |
| 11 | E | 0.77 | 1435 | — | 400 | 40 | 1 | 3.5 |
| 12 | F | 50 | — | 3.7 | 400 | 40 | 0.5 | 30.0 |
| 13 | F | 80 | — | 3.7 | 400 | 40 | 0.5 | 32.7 |
| 14 | F | 20 | — | 3.7 | 400 | 40 | 0.5 | 4.6 |
| 15 | F | 40 | — | 3.7 | 400 | 40 | 0.5 | 10.0 |
| 16 | F | 20 | — | 3.7 | 400 | 40 | 0.02 | 12.0 |

TABLE 3

| EX. # | activity (kgP/mol TMC hr) | activity (kgP/mol Act hr) | MW (wt. av) | MWD | % (CH$_2$)$_2$ | I.V. (dl/g) | Tm (C.) J/g |
|---|---|---|---|---|---|---|---|
| 1 | 346 | — | 5,100 | 1.86 | na | na | na |
| 2 | 26,986 | — | 723,700 | 1.85 | na | na | 129/0.31 |
| 3 | 60,145 | — | 1,255,400 | 1.90 | na | na | na |
| 4 | 31,771 | — | 1,318,700 | 1.96 | 10.6 | 10.26 | none |
| 5 | 92,695 | — | 1,824,100 | 1.77 | na | 19.28 | none |
| 6 | 9,251 | — | 693,200 | 1.95 | 12.1 | na | 123/0.29 |
| 8 | 7,156 | — | 391,000 | 1.80 | 16.3 | 3.63 | 123/0.08 |
| 9 | 21,989 | — | 229,500 | 1.81 | 15.7 | 2.26 | 122/0.55 |
| 10 | 15,829 | — | 520,900 | 2.45 | 13.7 | na | na |
| 11 | 956 | — | 197,700 | 1.91 | 13.5 | na | na |
| 12 | 1,674 | — | 355,400 | 1.74 | 3.8 | 3.59 | 122/0.31 |
| 13 | — | 1,200 | 308,200 | 3.27 | 14.9 | na | 122/0.22 |
| 14 | — | 1,300 | 359,300 | 3.05 | 15.0 | 3.29 | 123/0.24 |

TABLE 3-continued

| EX. # | activity (kgP/mol TMC hr) | activity (kgP/mol Act hr) | MW (wt. av) | MWD | % $(CH_2)_2$ | I.V. (dl/g) | Tm (C.) J/g |
|---|---|---|---|---|---|---|---|
| 15 | — | 740 | 167,800 | 1.81 | 13.6 | na | none |
| 16 | — | 800 | 115,400 | 1.67 | 14.2 | 1.27 | na |
| 17 | — | 57,573 | 838,700 | 2.31 | na | na | na |

TABLE 4

| EX # | mmmm | mmmr | rmmr | mmrr | mmrm + rmrr | mrmr | rrrr | rrrm | mrrm | m | r | B |
|---|---|---|---|---|---|---|---|---|---|---|---|---|
| 1 | 0.086 | 0.142 | 0.072 | 0.130 | 0.251 | 0.118 | 0.049 | 0.094 | 0.059 | 0.548 | 0.452 | 0.97 |
| 2 | 0.034 | 0.089 | 0.056 | 0.105 | 0.251 | 0.152 | 0.074 | 0.146 | 0.094 | 0.432 | 0.568 | 0.87 |
| 3 | 0.040 | 0.090 | 0.060 | 0.110 | 0.250 | 0.150 | 0.070 | 0.140 | 0.090 | 0.445 | 0.555 | 0.88 |
| 4 | 0.040 | 0.102 | 0.067 | 0.111 | 0.246 | 0.125 | 0.082 | 0.143 | 0.085 | 0.449 | 0.551 | 1.11 |
| 5 | 0.037 | 0.085 | 0.066 | 0.102 | 0.248 | 0.160 | 0.062 | 0.156 | 0.084 | 0.443 | 0.557 | 0.87 |
| 6 | 0.029 | 0.079 | 0.060 | 0.105 | 0.255 | 0.149 | 0.076 | 0.155 | 0.091 | 0.423 | 0.577 | 0.83 |
| 8 | 0.020 | 0.051 | 0.060 | 0.093 | 0.232 | 0.104 | 0.167 | 0.190 | 0.082 | 0.346 | 0.654 | 1.26 |
| 9 | 0.020 | 0.048 | 0.057 | 0.105 | 0.226 | 0.130 | 0.156 | 0.182 | 0.076 | 0.356 | 0.644 | 0.98 |
| 10 | 0.075 | 0.056 | 0.056 | 0.123 | 0.212 | 0.107 | 0.157 | 0.159 | 0.055 | 0.408 | 0.592 | 1.42 |
| 11 | 0.022 | 0.048 | 0.055 | 0.106 | 0.227 | 0.132 | 0.150 | 0.180 | 0.082 | 0.356 | 0.644 | 0.95 |
| 12 | 0.012 | 0.040 | 0.051 | 0.103 | 0.199 | 0.086 | 0.262 | 0.194 | 0.055 | 0.297 | 0.703 | 1.40 |
| 13 | 0.027 | 0.082 | 0.055 | 0.110 | 0.2469 | 0.142 | 0.077 | 0.158 | 0.103 | 0.413 | 0.587 | 0.89 |
| 14 | 0.027 | 0.078 | 0.056 | 0.107 | 0.2541 | 0.134 | 0.083 | 0.164 | 0.097 | 0.408 | 0.592 | 0.90 |
| 15 | 0.028 | 0.079 | 0.059 | 0.107 | 0.251 | 0.139 | 0.077 | 0.159 | 0.101 | 0.414 | 0.58 | 0.91 |
| 16 | 0.030 | 0.074 | 0.050 | 0.108 | 0.2488 | 0.144 | 0.074 | 0.158 | 0.115 | 0.403 | 0.597 | 0.85 |
| 17 | na | na | na | na | na | na | na | na | na | na | na | na |

TMC = transition metal compond
Al/M = aluminum/tranisition metal
Act/M = activator/transition metal
na = data not available

I claim:
1. A process for producing amorphous polypropylene comprising the steps of:
(i) contacting propylene under polymerization conditions with a catalyst system comprising;
(A) an activator, and
(B) a transition metal component represented by the formulae:

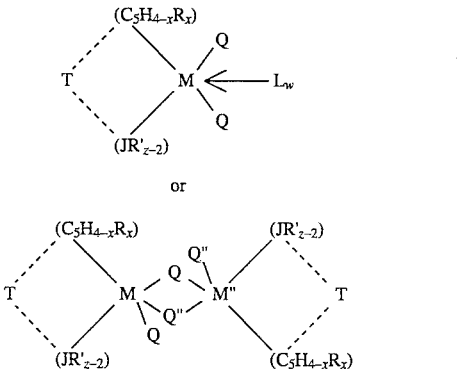

wherein M is Ti in its highest formal oxidation state;
$(C_5H_{4-x}R_x)$ is a cyclopentadienyl ring which is symmetrically substituted with zero, two or four substituent groups R, with "x" denoting the degree of substitution (x=2 or 4) and each R is, independently, a radical selected from a group consisting of $C_1-C_{20}$ hydrocarbyl radicals, substituted $C_1-C_{20}$ hydrocarbyl radicals wherein one or more hydrogen atoms is replaced by a halogen radical, an amido radical, a phosphido radical, an alkoxy radical or any other radical containing a Lewis acidic or basic functionality, $C_1-C_{20}$ hydrocarbyl-substituted metalloid radicals wherein the metalloid is selected from the Group IV A of the Periodic Table of Elements, and halogen radicals, amido radicals, phosphido radicals, alkoxy radicals, alkylborido radicals or a radical containing Lewis acidic or basic functionality, or at least two adjacent R-groups are joined forming $C_4-C_{20}$ ring to give a saturated or unsaturated polycyclic cyclopentadienyl ligand.

$(JR'_{z-2})$ is a heteroatom ligand in which J is an element with a coordination number of three from Group V A or an element with a coordination number of two from Group VI A of the Periodic Table of Elements, and each R' is, independently a radical selected from a group consisting of $C_1-C_{20}$ hydrocarbyl radicals, substituted $C_1-C_{20}$ hydrocarbyl radicals where one or more hydrogen atom is replaced by a halogen radical, an amido radical, a phosphido radical, and alkoxy radical or any other radical containing a Lewis acidic or basic functionality, and "z" is the coordination number of the element J;

each Q is, independently, a halide, hydride, or a substituted or unsubstituted $C_1-C_{20}$ hydrocarbyl, alkoxide, aryloxide, amide, or phosphide provided that where any Q is a hydrocarbyl, such Q is not a cyclopentadienyl or substituted cyclopentadienyl ligand, or both Q together are an alkylidene, or a cyclometallated hyrocarbyl or any divalent anionic chelating ligand;

T is a covalent bridging group containing a Group IV A or V A element;

M" has the same meaning as M, and Q" has the same meaning as Q;

L is a neutral Lewis base where "w" denotes a number from 0 to 3; and (ii) recovering amorphous polypropylene.

2. The process of claim 1 wherein the transition metal component is of the formula:

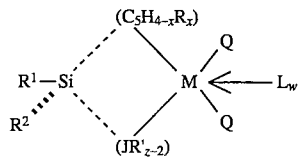

wherein $R^1$ and $R^2$ are, independently, a $C_1$ to $C_{20}$ hydrocarbyl radical, substituted $C_1$ to $C_{20}$ hydrocarbyl radical wherein one or more hydrogen atom is replaced by a halogen atom; $R^1$ and $R^2$ may also be joined forming a $C_3$ to $C_{20}$ ring.

3. The processes of claims 1 or 2 wherein the activator is alumoxane.

4. The processes of claims 1 or 2 wherein the activator is an ionic activator.

5. The processes of claim 2, wherein J is nitrogen.

6. The process of claim 1 wherein R is a $C_1$ to $C_{20}$ hydrocarbyl radical and R' is a $C_4$ to $C_{12}$ hydrocarbyl.

7. The process of claim 1 wherein R' is an alkyl radical or cyclic radical.

8. The process of claims 1 or 2 wherein x equals 4.

9. The process of claims 1 or 2 wherein Q is a hydrocarbyl or halide.

* * * * *